United States Patent
Linkous

(10) Patent No.: US 6,455,467 B2
(45) Date of Patent: *Sep. 24, 2002

(54) PHOTOCATALYTIC NUISANCE ORGANISM INHIBITOR AGENTS

(75) Inventor: Clovis A. Linkous, Merritt Island, FL (US)

(73) Assignee: University of Central Florida, Orlando, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 09/932,484

(22) Filed: Aug. 17, 2001

Related U.S. Application Data

(62) Division of application No. 09/491,051, filed on Jan. 25, 2000.

(51) Int. Cl.[7] .................. A01N 59/16; A01N 59/00; A01N 55/02; A01N 59/04
(52) U.S. Cl. .................. 504/120; 504/151; 504/152; 424/646; 424/617; 424/701
(58) Field of Search .................. 504/120, 151, 504/152; 424/617, 646, 701

(56) References Cited

U.S. PATENT DOCUMENTS

| | | | |
|---|---|---|---|
| 5,501,801 A | 3/1996 | Zhang | 210/748 |
| 5,547,823 A * | 8/1996 | Murasawa et al. | 430/531 |
| 5,880,067 A | 3/1999 | Linkous | 504/151 |
| 5,518,992 A | 5/1999 | Linkous | 504/151 |
| 5,994,992 A | 11/1999 | Linkous | 504/120 |

* cited by examiner

Primary Examiner—Alton Pryor
(74) Attorney, Agent, or Firm—Brian S. Steinberger; Law Offices of Brian S. Steinberger, P.A.

(57) ABSTRACT

Inexpensive, and easy to use self cleaning mixtures that use photoactive agents such as titanium dioxide($TiO_2$) and tungsten oxide($WO_3$) along with mixing the agents with co-catalysts such as carbon(C), Fe(iron), Cu(copper), Ni(nickel) and $CO_2P$. In addition, the co-catalyst loading can include up to approximately 5% carbon to maximize the inhibiting algae growth. The mixtures can be used to inhibit various growth organisms such as but not limited to algae, fungus, bacteria and mold. The agents can be combined together, and/or each agent can be combined with various coatings, such as but not limited to a cement or a polymer binder. The coatings can be applied to surfaces that are exposed to water such as but not limited to an aquarium, liners on the inner walls of swimming pools, drinking water tanks, and the like. Additionally, the coatings can be used as surfacing agent in contact with water within solar water heaters, piping adjacent to pool pumps, and the like. Additionally, the photoactive agent can be used as a non-toxic algae-retardant marine paint. Furthermore, the coatings can be applied to surfaces such as bathroom fixtures, toilets, bathtubs, sinks, and used on tiles in kitchens, bathrooms, and the like.

8 Claims, 3 Drawing Sheets

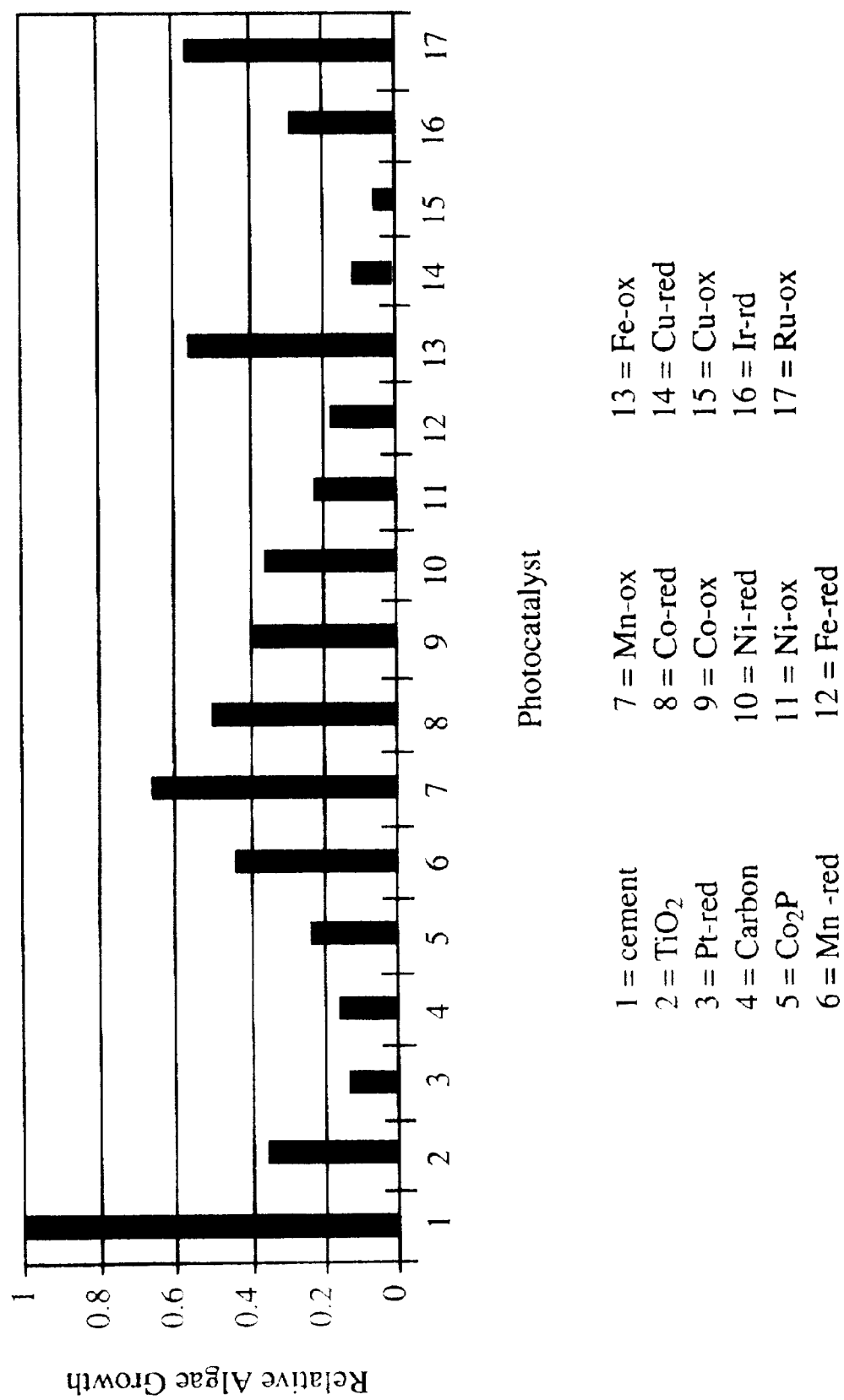

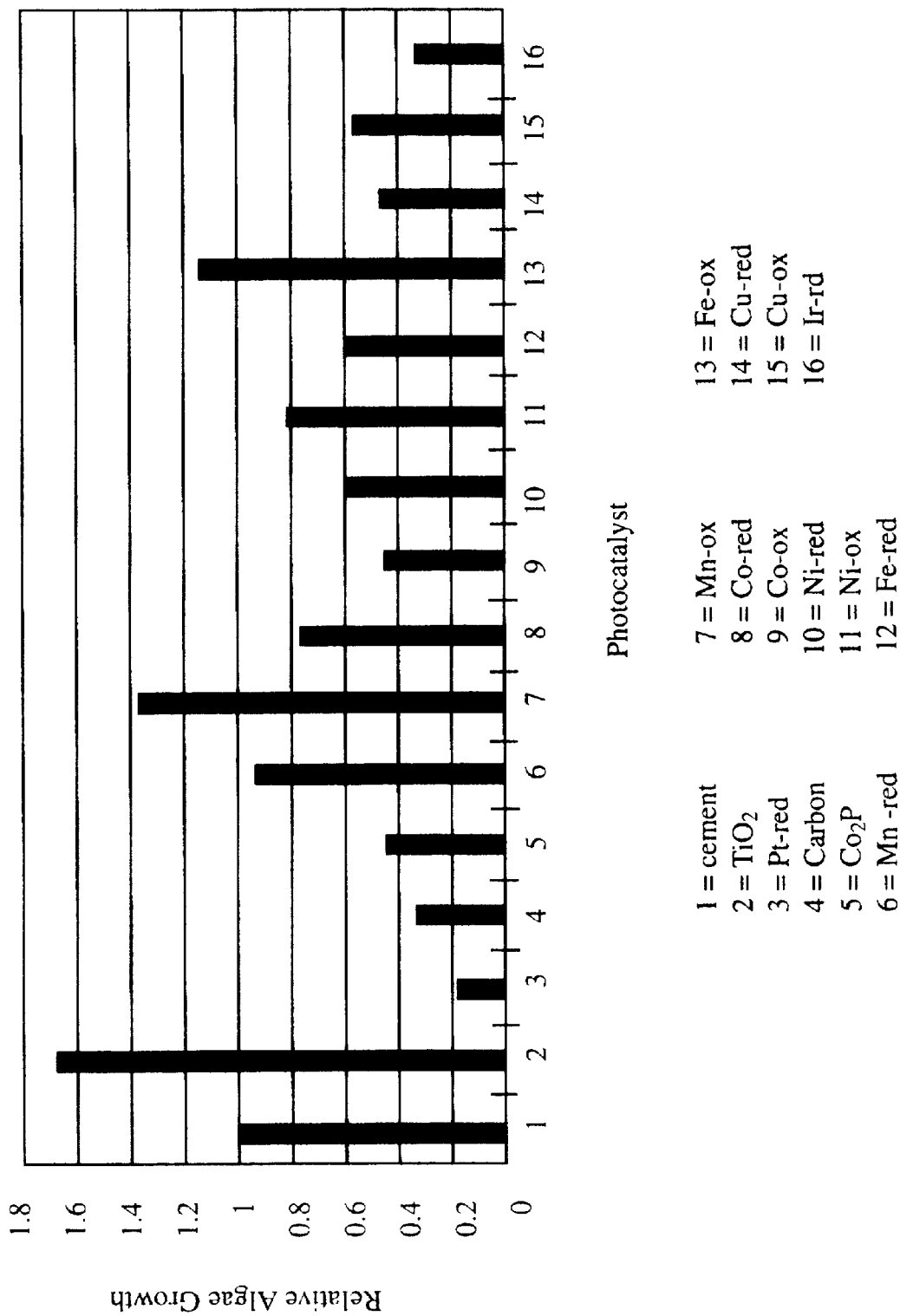
Figure 2. Realtive Algae Growth for M-WO$_3$ Photocatalyst.

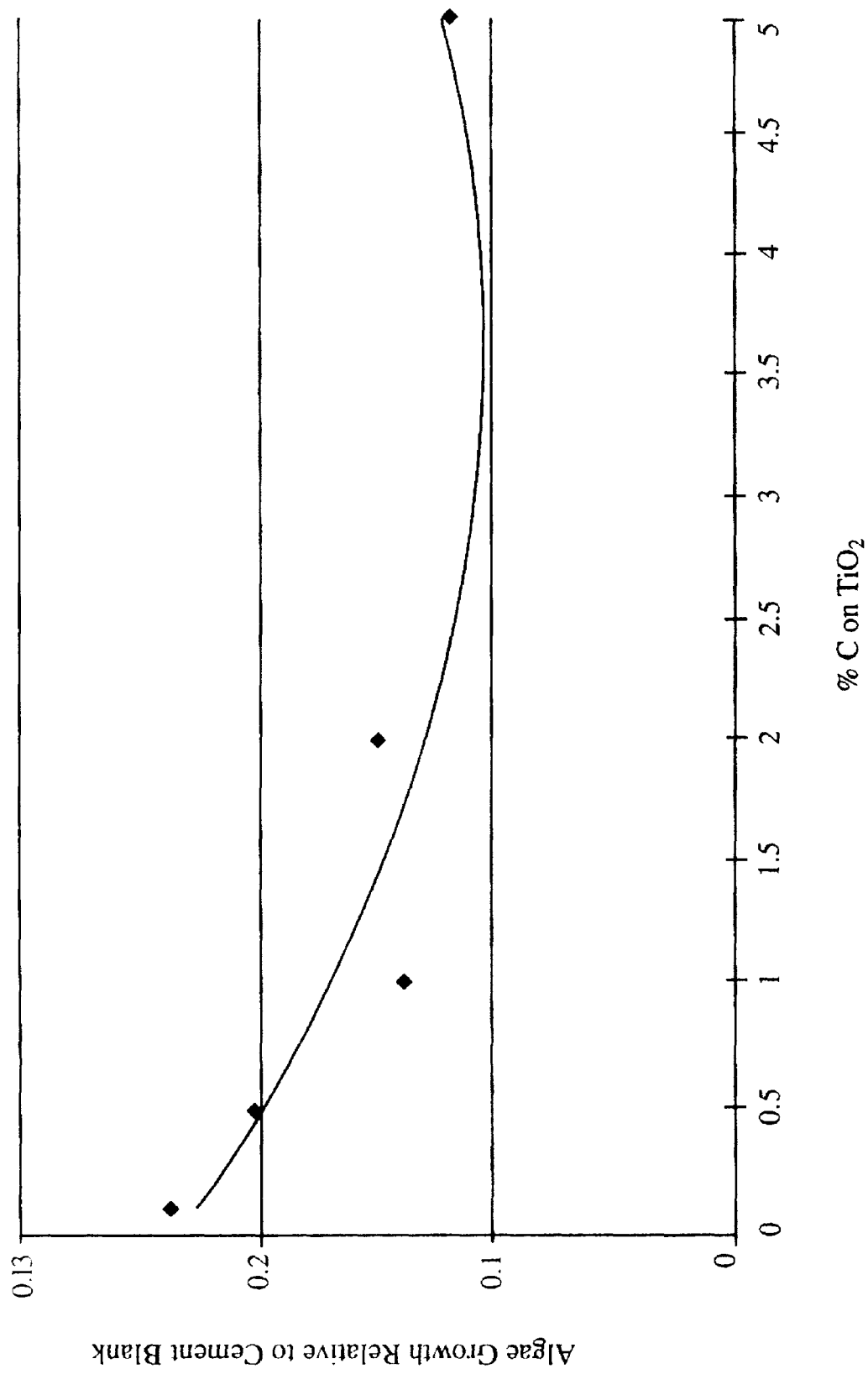
Figure 3. Algae Growth vs. % Carbon Loading

PHOTOCATALYTIC NUISANCE ORGANISM INHIBITOR AGENTS

This application is a division of 09/491,051 filed Jan. 25, 2000.

This invention relates to inhibiting the growth of fresh water and sea water plant life, and in particular to self cleaning photocatalytic surfacing agents and in particular to applying co-catalysts such as C, $Co_2P$, Co, Ni, Fe, Mn and Cu by various methods to photocatalysts such as $TiO_2$ (titanium dioxide) and $WO_3$ (tungsten oxide), and is a related to U.S. application Ser. No. 09/263,309 filed Mar. 5, 1999 to the same inventor and assignee and now issued as U.S. Pat. No. 5,994,268, which is a Divisional application of Ser. No. 08/859,348 filed on May 20, 1997, now issued as U.S. Pat. No. 5,880,067 to the same inventor and same assignee as this invention, both of which are incorporated by reference. This invention also relates to U.S. Pat. No. 5,518,992 issued on May 21, 1996 by the same inventor and same assignee thereof, whose subject matter is also incorporated by reference.

BACKGROUND AND PRIOR ART

Undesirable nuisance plant growth such as algae, bacteria, mold and fungus, have been a common problem for surfaces adjacent to freshwater and seawater areas. For example, swimming pools, fountains and other manmade vessels that hold water are subject to fouling by algae.

Past methods for preventing algae type plants have had numerous problems. Usual current surfacing agents for treating algae growth are generally toxins that can also be toxic to humans above threshold concentrations. For example, tributyl tin and cuprous oxide have been shown to be effective toxins and have been incorporated into marine paints for the hulls of boats. While the gradual release of toxins when the boat is underway can be acceptable, a boat in port can generate unacceptable concentrations of toxin.

Titanium Dioxide has been known to be used in commercial paint formulations and can be generally bright white in color. See for example, U.S. Pat. No. 5,142,058. However, these preparations are made deliberately so as to be photo-inactive where any form of photo-activity is regarded as a negative characteristic, because the organic binder containing the pigment can be ultimately attacked and destroyed.

A standard toxin agent is chlorine. Chlorine is a standard means for disinfecting both swimming pool water and drinking water. However, disinfectants such as chlorine become spent and must be replaced over time with repetitive additional costs. Heavy chlorination of microorganism containing water can also result in suspected carcinogenic by-products such as trihalomethanes.

Toxin release agents are not only inferior due to their health effects on higher order plants and animals, but also because they represent a consumable item that must be eventually replaced.

Many types of algaecides function as light blockers, absorbing the light necessary for algae growth. This involves dissolving one or more dyes in the water whose net absorption spectrum matches that of the algae. Thus, the water is dyed with an unnatural shade of blue or green that can be aesthetically unappealing. These algaecides are also subject to eventual decomposition and require periodic replenishment.

The subject inventor is aware of photocatalysts being used for the decomposition of organics. See U.S. Patents: U.S. Pat. No. 4,863,608 to Kawai; U.S. Pat. No. 5,244,811 to Matthews; U.S. Pat. No. 5,332,508 to Foster; U.S. Pat. No. 5,501,801 to Zhang; U.S. Pat. No. 5,541,096 to Nomura; U.S. Pat. No. 5,547,823 to Murasawa; U.S. Pat. No. 5,593,737 to Meinzer et al.; U.S. Pat. No. 5,616,532 to Heller et al. However, none of these photocatalysts use algae inhibiting co-catalysts to increase the decomposition of algae.

The subject inventor and assignee are also the same inventor and assignee of both U.S. Patents U.S. Pat. No. 5,518,992 entitled: Photocatalytic Surfacing Agents For Inhibiting Algae Growth and U.S. Pat. No. 5,880,067 Photocatalytic Surfacing Agents With Varying Oxides For Inhibiting Algae Growth, to the same inventor and same assignee as this invention. The '992 patent specifically deals with using platinum(Pt) as a co-catalyst for photocatalytic agents such as $TiO_2$ (titanium dioxide) and $WO_3$ (tungsten oxide). While, platinum is an excellent co-catalyst it is also a very expensive material costing for example $400/oz. Thus even though the co-catalyst is present at only a 1.0% by weight loading, at $400.00 per ounce, even as a bulk commodity, the Pt would comprise 98% of the cost of the photocatalyst. Previous work has shown that the minimum coverage of photocatalyst to achieve an optimized photo effect across a surface is about 1.0 $mg/cm^2$. Pure Anatase $TiO_2$ costs about $1.00/lb. Therefore, the photocatalyst cost to cover 100 $m^2$ with plain $TiO_2$ would only be $2.20. On the other hand, if the $TiO_2$ were to be modified with 1.0% by weight of Pt, the cost of the photocatalyst would rise to $141.00. Clearly there is strong motivation to find a less expensive yet effective, co-catalyst.

SUMMARY OF THE INVENTION

The first objective of the present invention is to provide photocatalysts with co-catalysts as surfacing agents for inhibiting nuisance organisms such as algae, bacteria, mold and fungus.

The second object of this invention is to provide photocatalysts with co-catalysts as surfacing agents for inhibiting nuisance organisms that are nontoxic.

The third object of this invention is to provide photocatalysts with co-catalysts as surfacing agents for inhibiting nuisance organisms that becomes active and remains active when light is applied.

The fourth object of this invention is to provide photocatalysts with co-catalysts as surfacing agents for inhibiting nuisance organisms that becomes active and remains active when light is applied.

The fifth object of this invention is to provide photocatalysts with co-catalysts as surfacing agents for inhibiting nuisance organisms that does not need constant replacement nor replenishment to remain active.

The sixth object of this invention is to provide photocatalysts with co-catalysts as surfacing agents for inhibiting nuisance organisms without coloring water with algacidal dyes.

The seventh object of this invention is to provide photocatalysts with co-catalysts as surfacing agents for inhibiting nuisance organisms that has a one-time economical cost.

Embodiments of the invention include mixing a catalyst of titanium dioxide or tungsten oxide with carbon, $Co_2P$, Co, Ni, Fe, and Cu.

Further objects and advantages of this invention will be apparent from the following detailed description of a presently preferred embodiment which is illustrated schematically in the accompanying drawings.

BRIEF DESCRIPTION OF THE FIGURES

FIG. 1 is a bar graph comparison of Algae growth of using various co-catalysts with catalytic agent $TiO_2$ (titanium dioxide).

FIG. 2 is another bar graph comparisons of Algae growth of using various co-catalysts with catalytic agent $WO_3$ (tungsten oxide).

FIG. 3 shows a graph of algae growth vs. % Carbon loading on $TiO_2$ (titanium dioxide).

DESCRIPTION OF THE PREFERRED EMBODIMENT

Before explaining the disclosed embodiment of the present invention in detail it is to be understood that the invention is not limited in its application to the details of the particular arrangement shown since the invention is capable of other embodiments. Also, the terminology used herein is for the purpose of description and not of limitation.

The inventor of the subject invention in U.S. Pat. No. 5,518,992 to Linkous, which has been incorporated by reference, has shown that $WO_3$ (tungsten oxide) have been shown to be useful as a photocatalytic surfacing agent for inhibiting algae growth along with using Platinum(Pt) as a co-catalyst for both ($TiO_2$ (titanium dioxide) and $WO_3$ (tungsten oxide).

U.S. Pat. No. 5,880,067 to Linkous, which is also incorporated by reference, has shown that combining either ($TiO_x$(titanium dioxide) or $WO_x$ (tungsten oxide) with the oxide number being variable, and a noble metal chosen from Pt(platinum), Ir(iridium), Pd(palladium), Au(gold), Ru(ruthenium) or Os(osmium), are also useful as photocatalytic surfacing agents for inhibiting algae growth. Both U.S. Pat. Nos. 5,518,992 and 5,880,067 are assigned to the same assignee as the subject invention.

Table 1 shows Average Algae Growth Rates on Various Photocatalyst Preparations Relative to Plain Cement. The number of tests are given in the parentheses. The tests were conducted at the Florida Solar Energy Center, Cocoa, Fla. from Jun. 19, 1998 to Nov. 4, 1999.

The chlorophyll content was determined by a simplified method based on that of Lorenzen (C. J. Lorenzen, "Determination of chlorophyll and pheo-pigments: spectrophotometric equations," Limmol.Oceanogr. 12 (1967) 343–346.) In this method, the biomass is thoroughly ground, extracted with alkaline acetone solution, and centrifuged down to yield a clear yellow-green solution. After making a baseline correction for any residual turbidity, chlorophyll content is determined by the absorbance at 665 nm. An additional step to correct for the light absorption of phaeophytims, naturally occurring degradation products of chlorophyll, was deemed unnecessary, as the relative amounts of chlorophyll and phaeophytin in each sample were thought to be constant.

For the tests, a swimming pool surface-grade cement, also known as Pool-Kote®, and a mixture of crushed white marble and Portland cement, was cast in to 2"×2"×¼" substrates. These were coated with a binder/photocatalyst formulation consisting typically of 10% binder by weight. Coated substrates were tested by standing on a narrow plastic shelf immersing in the algae tank, and irradiating with a horizontally positioned light bank. The light bank consisted of 4 bulbs, 2 black light and 2 conventional fluorescents. The fluorescent lights provided long wavelength light, across the visible spectrum from approximately 400 nm to approximately 700 nm, to principally stimulate algae growth, while the black lights supplied short wavelength, near-ultraviolet light to activate the photocatalyst. The spectral outputs of these lamps are shown in U.S. Pat. No. 5,518,992 which is incorporated by reference. The radiant power of each light source was approximately equal.

Table 1 gives the Algae Growth Rates on Various Photocatalyst Preparations relative to Plain Cement, with the mixed light source; and number of tests shown in parentheses.

TABLE 1

Algae Growth Rates on Various Photocatalyst Preparations Relative to Plain Cement

| co-catalyst | $TiO_2$ | $WO_3$ | $TiO_x$ | $WO_x$ |
|---|---|---|---|---|
| none | 0.342 (10) | 1.67 (3) | 0.575 (3) | 1.01 (4) |
| Pt-red | 0.129 (3) | 0.186 (3) | .083 (4) | 0.695 (3) |
| carbon | 0.140 (4) | 0.307 (5) | 0.572 (5) | 0.712 (5) |
| $CO_2$ | 0.224 (4) | 0.429 (4) | 0.618 (4) | 0.992 (3) |
| Mn-red | 0.447 (3) | 0.949 (2) | N/A | N/A |
| Mn-ox | 0.644 (3) | 1.37 (2) | N/A | N/A |
| Co-red | 0.489 (3) | 0.766 (2) | 0.534 (3) | 1.03 (3) |
| Co-ox | 0.395 (4) | 0.441 (3) | N/A | N/A |
| Ni-red | 0.356 (3) | 0.583 (2) | 0.502 (3) | 1.02 (3) |
| Ni-ox | 0.208 (4) | 0.812 (3) | N/A | N/A |
| Fe-red | 0.168 (3) | N/A | N/A | N/A |
| Fe-ox | 0.533 (4) | 1.13 (3) | N/A | N/A |
| Cu-red | 0.112 (3) | 0.462 (3) | 0.318 (3) | 0.114 (3) |
| Cu-ox | 0.063 (3) | 0.552 (3) | N/A | N/A |
| Ir-red | 0.288 (3) | 0.315 (3) | N/A | N/A |
| Ru-ox | 0.548 (2) | N/A | N/A | N/A |

$TiO_2$ refers to titanium dioxide. $WO_3$ refers to tungsten oxide. $TiO_x$ refers to titanium dioxide blend and $WO_x$ refers to tungsten oxide blend. mixed light source; number of tests shown in parentheses Prepared samples were placed in an algae-rich environment for one week. The extent of algae growth on each substrate as then determined by quantifying the amount of chlorophyll contained in the algae cells. The amount of algae biomass that had grown was directly proportional to the amount of chlorophyll.

The algae consisted of one or more species from the genus Oedongonium, filamentous algae that propagate and spread themselves onto a new surface by attachment of motile zoospores, which anchor and begin growth of a new filament. This is a common fresh water green algae found in lakes and streams, and also in aquariums. Its ability to quickly spread from one surface to another through clear, open water made it an ideal species to use in testing the photocatalytic formulations.

In Table I, data for 4 photocatalysts and 15 co-catalysts are given. The numbers represent algae growth relative to an unprotected substrate, i.e., a bare cement substrate that had not been coated with photocatalyst. In nearly all instances, a reduction in algae growth was observed (ratio <1.00)

In Table 1, a low number means algae prevention, a high number generally goes to the less the effect of algae prevention. The 0.342 value for plain titanium dioxide, and the 1.67 value for plain tungsten oxide represents a baseline for comparison of the co-catalysts. The numbers in parentheses are the number of test runs made to obtain the average value for each formulation. Each transition metal co-catalyst has two rows because we had two methods of depositing it.

In one deposition method, the photocatalyst was suspended briefly in a solution containing a metal salt. The photocatalyst was then collected by filtration and calcined in an oven at 450° C. for 6 hours. The co-catalyst is thus attached as a metal oxide deposit on the photocatalyst surface. Co-catalysts attached in this way are designated "ox". In another method, the photocatalyst is suspended in a metal salt solution and then added to a solution of a reducing agent such as sodium borohydride, NaBH4. The borohydride ion reduces the metal ions in solution, depositing them onto the suspended particulates. The photocatalyst is then collected and dried in a low temperature over (120° C). Co-catalysts attached in this way are designated "red".

Several conclusions can be made. While nearly all the formulations shown in Table 1 are ostensibly photocatalytic, both the reduced oxides and $WO_3$ lag behind $TiO_2$ (shown in the first column). From Table 1, it is clear that carbon black(C) can be substituted for platinum(Pt) as a co-catalyst and achieve approximately the same level of algae inhibition. Carbon is less costly than platinum.

On a weight basis, carbon costs less than $TiO_2$, on order of $60–600 per ton, depending on purity and morphology, so that the cost of the photocatalyst would be scarcely affected by including carbon. This is in sharp contrast to Pt, where a 1% loading would increase the price over 60-fold.

Using carbon as a co-catalyst gives an affordable, blue grey to black-colored formulation that inhibits algae significantly better than plain $TiO_2$. A form of Carbon that can be used includes Vulcan XC72 made by Cabot Corporation.

A 1.0% by weight sample of $TiO_2$ has a slate or blue-gray color. Increasing carbon content results in the sample becoming increasingly darker. A 2% sample is dark gray, and a 5% C—$TiO_2$ sample is quite black.

As shown in FIG. 3, increasing carbon content also accrues a performance improvement up to 5% carbon. However, since the performance ration for a pure carbon sample is 0.438, greater than that of plain $TiO_2$, too high a carbon content can be counter-productive.

As seen in Table 1, a number of transition metal-based co-catalyst formulations were also tested. Manganese, cobalt, iron, nickel, copper and ruthenium are among the new materials. Data for unmodified $TiO_2$ and previously patented co-catalyst Pt, Ir, and $Co_2P$ are also given. The value 0.342 as the algae growth rate on a $TiO_2$-coated surface relative to plain cement provides a benchmark for comparison with the co-catalyst formulation. $TiO_2$ photocatalyst modified with co-catalysts Ni-ox, Fe-red, Cu-ox, Cu-red, and Ir-red were found to inhibit algae growth to an even greater extent.

As for $WO_3$, all the co-catalysts had a beneficial effect, since unmodified $WO_3$ itself displays a negative effect, i.e., algae growth is more vigorous on it than on plain cement. On the other hand, only three $WO_3$ formulations (Pt—$WO_3$, C—$WO_3$, and Ir—$WO_3$) displayed better activity than unmodified $TiO_2$.

As seen in Table 1, the results for Cu(copper) as a co-catalyst appeared to be spectacular, and better than those for Pt(platinum).

It was thought necessary to establish whether the new photocatalysts were effective because they were more photocatalytic, or because of morphological or toxicological effects instead. A new set of tests were instigated with fluorescent light only. With a much diminished UV component of the spectral irradiance, it was expected that a true photocatalyst would perform poorly, since it would be absorbing very little light. These results are shown in Table II. As expected, most of the photocatalysts performed worse than with the black light. Many were essentially the same as unmodified $TiO_2$, with a relative growth rate of 0.584. One of the exceptions was Fe, which showed a pronounced negative effect, with a relative growth rate of 0.963. This means that the effect of Fe as an algae-inhibiting modifier of $TiO_2$ is negative under low light intensity conditions, but positive in bright light with a significant UV component. On the other hand, Cu continued to show positive effects without near-UV irradiance. This is evidence that Cu has a toxicological effect on algae in addition to any photocatalytic effect.

TABLE II

Relative Algae Growth under Fluorescent Lamp Only

| $TiO_2$ sample | trial 1 | trial 1 | trial 3 | trial 4 | average |
|---|---|---|---|---|---|
| unmodified | 0.448 | 0.712 | 0.611 | 0.564 | 0.584 |
| Cu-red | 0.196 | 0.112 | N/A | N/A | 0.103 |
| Cu-ox | 0.034 | 0.098 | 0.088 | N/A | 0.073 |
| Fe-red | 1.09 | 1.11 | 0.941 | 0.712 | 0.963 |
| $Co_2P$ | 0.378 | 0.434 | 0.618 | 0.658 | 0.522 |
| C | 0.703 | 0.500 | 0.375 | 0.762 | 0.585 |
| Ni-red | 0.538 | N/A | N/A | N/A | 0.538 |
| Ni-ox | 0.282 | 0.322 | 0.282 | 0.730 | 0.404 |

Ni and Fe also appear to be worth being used for algae inhibition since they represent enhanced photoactivity, cheap materials, and new colors(pale green and orange, respectively).

Ni and Fe are both relatively inexpensive materials. The colors or tints they impart as co-catalysts to $TiO_2$ can also find value as an aesthetic attribute over the white background otherwise supplied by the $TiO_2$.

The novel photoactive mixtures can be used to inhibit various growth organisms such as but not limited to algae, fungus, bacteria and mold. The agents can be combined together, and/or each agent can be combined with various coatings, such as but not limited to a cement or a polymer binder. The coatings can be applied to surfaces that are exposed to water such as but not limited to an aquarium, liners on the inner walls of swimming pools, drinking water tanks, and the like. Additionally, the coatings can be used as surfacing agent in contact with water within solar water heaters, piping adjacent to pool pumps, and the like. Additionally, the photoactive agent can be used as a non-toxic algae-retardant marine paint. Furthermore, the coatings can be applied to surfaces such as bathroom fixtures, toilets, bathtubs, sinks, and used on tiles in kitchens, bathrooms, outdoors on walls and roof tops, and the like.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

I claim:

1. A method of inhibiting the growth of nuisance organisms on surfaces using a photocatalytic coating, comprising the steps of:
    (a) applying a coating consisting of at least one of $TiO_1$ and $WO_2$, wherein $0<n1\leq2$ and $0<n2\leq3$, and a photocatalyst solely consisting of Carbon(C) black as a co-catalyst, to a surface, and wherein the photocatalyst with the Carbon black co-catalyst has a Carbon content weight of approximately 0.1% to approximately 2% Carbon black; and
    (b) applying light to the coating which becomes photoactive to inhibit the growth of nuisance organisms on the surface.

2. The method of inhibiting the growth of nuisance organisms of claim 1, wherein: n1 equals 2, and n2 equals 3.

3. The method of inhibiting the growth of nuisance organisms of claim 1, further comprising the steps of:
    exposing the surface to at least one of: water, humid air, and water vapor.

4. A method of inhibiting the growth of nuisance organisms, comprising the steps of:

mixing a photocatalyst consisting of at least one of $TiO_{n1}$ and $WO_{n2}$, wherein $0<n1 \leq 2$ and $0<n2\leq 3$ with a co-catalyst solely consisting of Carbon(C) black, wherein the Carbon black weight of the mixture is approximately 0.1% to approximately 2% Carbon black;

applying the mixture to a surface; and exposing the mixture to light, wherein the mixture which becomes photoactive to inhibit the growth of nuisance organisms on the surface.

5. The method of claim 4, wherein:

n1 equals 2, and n2 equals 3.

6. The method of claim 4, further comprising the steps of:

exposing the surface to at least one of: water, humid air, and water vapor.

7. A photocatalytic coating for inhibiting nuisance organism growth on surfaces, consisting of in combination:

a photocatalyst consisting of at least one of $TiO_{n1}$ and $WO_{n2}$, wherein $0<n1 \leq 2$ and $0<n2\leq 3$;

a co-catalyst mixed with the photocatalyst, the co-catalyst solely consisting of carbon (C) black as the co-catalyst, the mixture of the photocatalyst and the co-catalyst has a carbon content weight of approximately 0.1% to approximately 2% Carbon(C) black;

a surface for the coating of the photocatalyst and the co-catalyst to be applied thereto; and means for applying light to the coating so that the coating becomes photoactive to inhibit the growth of nuisance organisms on the surface.

8. The photocatalytic coating of claim 7, wherein n1 equals approximately 2, and n2 equals approximately 3.

* * * * *